United States Patent [19]
Cella et al.

[11] Patent Number: 5,120,709
[45] Date of Patent: Jun. 9, 1992

[54] METHOD FOR ENHANCING FRAGRANCE APPLICATIONS

[75] Inventors: John A. Cella, San Diego; John A. Cella, III, La Mesa, both of Calif.

[73] Assignee: Neuroscents, Inc., La Mesa, Calif.

[21] Appl. No.: 596,801

[22] Filed: Oct. 12, 1990

[51] Int. Cl.⁵ ............................................. A61K 7/46
[52] U.S. Cl. .............................................. 512/2; 512/3
[58] Field of Search ........................................ 512/2.3

[56] References Cited

U.S. PATENT DOCUMENTS 3,415,813 12/1968 Thomas .................................. 512/5
4,162,221 7/1979 Durr et al. ............................. 512/2

OTHER PUBLICATIONS

Berends, W. *American Perfumer and Cosmetics* 80:35-38 (1965).

Carpenter, M. and Easter, W., *Journal of Organic Chemistry*, 19:77-87 (1954).

Carpenter, M. and Easter, W., *Journal of Organic Chemistry*, 16:618-620 (1951).

*Primary Examiner*—James H. Reamer
*Attorney, Agent, or Firm*—Knobbe, Martens, Olson & Bear

[57] ABSTRACT

Compositions and methods for enhancing the quality of applied fragrances by means of a fixative agent. The fixative agent may be a nitro musk, or a macrocyclic, hydroaromatic polycyclic, or oxahydroaromatic compound. The fixative is applied independently, in a separate application from that of the fragrance form. The method imparts the body, richness and persistence of perfume fragrances to less costly fragrance forms, such as colognes.

9 Claims, No Drawings

METHOD FOR ENHANCING FRAGRANCE APPLICATIONS

BACKGROUND OF THE INVENTION

The invention relates to the art of perfumery, and particularly to methods for employing fragrances.

Fragrances are marketed in a variety of forms, the most common form being a solution of essential oils in ethyl alcohol. The characteristic scent of a particular fragrance is determined by the balance of its unique mixture of essential oils. Essential oils comprise organic compounds having a pleasant scent, and designated, in broad terms, according to their volatility, as top notes (most volatile), middle notes (intermediate volatility), and base notes or fixatives (low volatility).

Fragrances are manufactured in varying concentrations of essential oils in alcohol and other organic solvents, designated in increasing order of concentration as eau de toilette, after shave, or toilet water, 2-5%; eau de cologne or cologne, 5-10%; eau de parfum or eau de perfume, 11-15%; and parfum or perfume 16-50%. Users perceive perfume to be richer, more full-bodied than a less concentrated cologne, and when applied to skin, perfume emits a stronger, more persistent scent. Typically, the price of perfume is 3-10 times that of eau de perfume, 10-15 times that of cologne, and 15-20 times that of eau de toilette. A manufacturer usually markets a perfume and a lower priced cologne version of the same fragrance. Both have the same overall fragrance character, but the perfume version will contain more expensive, more complex essential oils, including more fixatives.

Fixatives have an important role in the complex art of perfumery. The earliest known fixatives were natural musks, such as that obtained from the musk deer. Crude extracts from the musk deer and civet cat were prized historically as ingredients indispensable to the manufacture of fine fragrances. The chemical isolation and characterization of the active compounds of the animal musks, muskone and civetone, indicated that these materials were macrocyclic compounds, having seven or more carbon atoms in a ring. Musk from the ox was found to be methyl-substituted-cyclopentadecanone, and that of the civet cat unsaturated cycloheptadecanone. Similar musk-like substances were later found in angelica root oil and ambrette seed. These natural musks of vegetable origin were found to be macrocyclic lactones. Angelica root oil contains cyclopentadecanolactone and ambrette seed oil contains ambrettolide, 7-cyclohexadecanolactone. Early chemists believed that in vitro synthesis of such compounds would be exceedingly difficult because of the instability of the ring structures. Accordingly, natural musks of both animal and vegetable origin commanded a high price.

However, in 1888 the chemist Baur found that a nitrobenzene compound, 2,4,6-trinitro-3-methyl-tert-butylbenzene possessed a strong musk odor, and several nitrobenzene compounds having a musk character were subsequently synthesized. Musk perfumes were also found in synthetic compounds having other chemical structures, such as steroid (16-androsten-3-ol), indane, benzene, and tetralin types (Berends, W. *American Perfumer and Cosmetics* 80:35-38 (1965). Chemists also discovered that large macrocyclic structures are not inherently unstable, because valence bond angles can be maintained if the ring assumes a non-planar configuration, and synthetic fixatives of this class were made. Thus several classes of synthetic compounds useful as fixatives became available and these were also designated musks, by derivation and analogy to the original animal extract.

A structure-odor relationship among fixative compounds has not been fully determined. It is suggested that the common characteristics of useful compounds are that they have (1) a molecular weight of 200-300; (2) a compact molecular structure; and (3) a functional group. This broad definition accommodates several chemical classes.

The most important class of musks are macrocyclic compounds, having from: 15-20 ring atoms and at least one functional group. Among this group there are at least five types: lactones, ketones, carbonates, anhydrides, and cyclic oxides, sulfides and amines. Another class is that of the nitro musks. Of all the nitro musks synthesized since Baur, only five are in commercial use today: Musk Xylene, Musk Ambrette, Musk Tibetene ™, Musk Ketone, and Moskene ™ (Givauden Corp., Delawanna, New Jersey). All comprise a benzene structure substituted with 2-3 $NO_2$ groups, 1-3 $CH_3$ groups, and a tert-butyl group (Carpenter, M. and Easter, W. *J. Organic Chemistry* 19:77,87 (1954). A third class is that of the hydroaromatic polycyclics, comprising the indane type having the basic structure (I); the steroid type, having the basic structure (II); and the tetralin type, having the basic structure (III). Yet another class is that of the oxahydroaromatics, having a basic structure such as (IV).

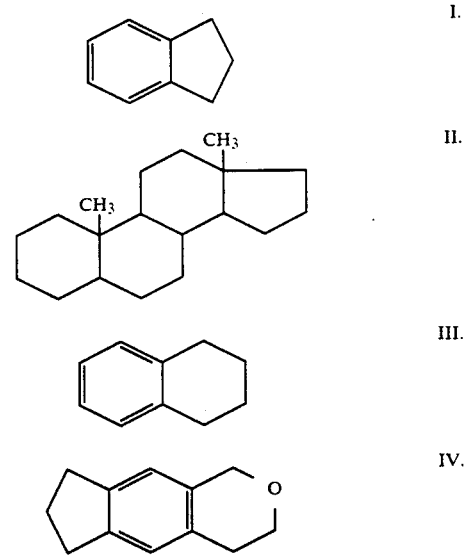

Although the musk-like fixative compounds have a wide range of pleasant odors, they are used in perfumery not particularly for this property, but for their ability to impart a refinement to luxury perfumes which is subjective and therefore difficult to define. This contribution has been expressed, however as "fixation," "exaltation," "rounding," or "cachet," as well as "noble," and "luxurious."

It would be desirable to enjoy these characteristics ordinarily found only in fragrances of the expensive luxury perfumes while using less costly products. It would also be desirable to have a product which would convert any fragrance into its perfume counterpart. Accordingly it is an object of the invention to provide a method to enhance the properties of colognes and other lower priced fragrance preparations having lower concentrations of essential oils to make them comparable to perfumes at a cost savings to the consumer.

SUMMARY OF THE INVENTION

According to one aspect of the invention there are provided compositions consisting essentially of a mixture of at least two fragrance-enhancing fixative agents in a volatile solvent. The application of the composition together with a fragrance form according to the methods of the invention enhances the scent of said fragrance form without perceptible distortion, making it richer, fuller, and more attractive as well as increasing its persistence.

According to another aspect of the invention there is provided a method for enhancing the effect of an applied fragrance form by the co-application of a fixative agent. In a preferred application, the fixative is independently applied to the same area as the fragrance form. In a particularly preferred embodiment, the fixative agent is applied by overspraying a composition comprising the fixative in a volatile solvent to the area in which the fragrance form has been applied. The fragrance form and the fixative composition are typically applied to human skin.

The fragrance form to be enhanced by the co-application of a fixative agent can be a commercial product which is an eau de toilette, after shave, toilet water, eau de cologne, cologne, eau de parfum or eau de perfume.

The fixative agent that is used in the compositions and methods of the invention can be selected from either natural or synthetic fixative agents. It can accordingly be a nitro musk, or a macrocyclic, hydroaromatic polycyclic, or oxahydroaromatic compound or a combination thereof. Preferred fixative agents are galaxolide (IFF), ethylene brassylate, 4-acetyl-6-t-butyl-1,1-dimethylindane, 11-oxahexadecanolide, musk ambrette, musk ketone, musk xylol, civetone or androstene-one or a combination thereof. A preferred combination of fixative agents is galaxolide, ethylene brassyla te, 4-acetyl-6-t-butyl-1,1-dimethylindane, and 11-oxahexadecanolide in a ratio of 1:2:2:2 by weight.

For use according to the methods of the invention, the fixative agent can be dissolved in a volatile solvent or a combination of such solvents. Preferred solvents are ethanol (39C), volatile silicones, diethyl phthalate, and benzyl benzoate.

DETAILED DESCRIPTION OF THE PREFERRED EMBODIMENT

We have discovered that a fixative compound or a mixture of such compounds can be used to enhance the body, richness, and persistence of weaker, less costly fragrance forms, such as colognes, eau de toilettes, and eau de parfums, and to impart to those fragrance forms the properties of their more expensive perfume counterparts.

Surprisingly, fixative compositions used according to the method of the invention do not significantly shift or distort the character of the fragrance or impart a fragrance of their own. Instead, an appropriate fixative preparation applied together with a low quality fragrance will not only make it longer lasting, but also smell richer, more full-bodied, and be perceived to have the scent and character of more costly fragrance forms such as perfume.

The addition of fixative to cologne does not reconstitute a perfume, but enhances the cologne so as to creates an illusion of the perfume. The difference between a cologne and a corresponding perfume is not only in the total concentration of essential oils, but in the quality and complexity of those materials. The oils used in perfumes are usually an extract or distillate of a natural fragrance source. A classic example of a precious perfume oil is Bulgarian rose attar, extracted from rose flowers, and prized for its strong, full-bodied rosy aroma. Bulgarian rose attar is a composite of over 50 organic compounds; it costs about $2000 per pound. Geraniol is a unique organic compound, trans-3,7-dimethyl-2,6-octadien-1-ol, that has a sweet rosy odor, and can be found in oils extracted from roses, geraniums, palmarosa and citronella. It can be prepared synthetically for about $20 per pound. Geraniol and Bulgarian rose attar in alcoholic solution both have the aroma of roses, but the rose attar aroma is richer and fuller, and is perceived as more expensive and finer by the user. In an olfactory sense, the natural rose fragrance is polydimensional, while the geraniol rose fragrance is not.

The valuable property of fixatives is that, even though they are single organic compounds, they have polydimensional olfactory characteristics. Thus, in addition to having a "musky" (otherwise characterized as "animal" or "amber") odor, they also have some of the olfactory characteristics of other essential oils. A member of the perfume industry, Naarden (N.V. Chemische Fabriek Naarden, Holland), has created a computerized odor profile which classifies and quantifies the characteristics and strengths of a particular musk according to 11 categories. Categories are named fresh, earthy, fruity, animal, floral, sweet, spicy powdery, amber, woody and balsamic. One of Naarden's musks, Musk R1, shows significant "notes" in seven of the eleven categories. This musk then has the ability to augment the fragrance notes of a cologne preparation which are common to both.

A suitable fixative agent is a compound that acts to enrich the olfactory stimulation produced by the fragrance, without changing its overall character. Olfactory perception is subjective and complex, but not unpredictable. To achieve an optimal effect, some difficulties must be avoided. For example, if the musk or fixative is relatively concentrated with respect to the fragrance it is to enhance, the balance of the notes in the fragrance will be distorted; therefore the ratio of fixative to fragrance applied must be controlled. This can be achieved by preparing the optimal concentration of fixative and applying it to an area in a metered spray application. Although fragrances are shifted in scent somewhat on application to different individuals, and the olfactory discrimination varies from person to person, the augmented fragrance as perceived is reasonably reproducible. Balanced against subjective olfactory perception is the relative inability of most persons to discriminate precisely among scents. For these reasons the fixative-augmented cologne is reliably perceived as the more expensive fragrance. The fixative also enhances the fragrance by reducing the rate of diffusion of the fragrance from the surface, thus making the effect of the fragrance last longer.

The fragrance-enhancing compositions of the invention can be comprised of one or more natural or synthetic fixatives or musks, but is not limited to such ingredients. Any suitable fixative or combination of fixatives may be selected to accomplish the desired result of enhancing the body, richness and persistence of a fragrance application. In preferred embodiments, the fixatives are selected from the following groups of organic materials: 1) nitro musks, 2) macrocyclics, 3) hydroaromatic polycyclics, and 4) oxahydroaromatics. Preferred nitro musks comprise musk ambrette (6-t-butyl-3-methyl-2,4-dinitroanisole), musk ketone (4-t-butyl-3,5-dinitro-2,6-dimethylacetophenone), and musk xylol (2,4,6-trinitro-1,3-dimethyl-5-t-butylbenzene); preferred macrocyclics comprise ethylene brassylate (5,17-diketo-1,4-dioxa-cycloheptadecane), 11-oxahexadecanolide, and civetone (9-cycloheptadecene-1-one); preferred hydroaromatic polycyclics comprise 4-acetyl-6-t-butyl-1,1-dimethylindane; preferred oxahydroaromatics comprise 3,4,5,6,7,8-hexahydro-4,6,6,7,8,8-hexamethyl-3,4-cyclopenta-2-benzopyran (galaxolide, IFF). The chemical structures of fixatives suitable for use in the preparations and methods of the invention are presented in the Appendix.

Although it is possible to practice the methods of the invention by using a solution of a single fixative, best results are achieved when combinations of fixatives are used because there is a wide variation in the ability of different individuals to smell musky fixative materials; a single fixative might be undetectable to some, and at the same time overwhelming to others. Combining fixatives overcomes this difficulty.

A selection of an appropriate fixative or combination of fixatives to be used in the fragrance-enhancing preparation and methods of the invention is made by matching the olfactory profile of the fixative to the characteristics of the fragrance or class of fragrance to be applied. An olfactory profile comprises characteristic fragrance notes which can be recognized by those skilled in the art by subjective evaluation; alternatively this information is published by manufacturers of fixatives. Profiles of selected fixatives according to the Naarden basis of classification are listed in Table 1a. Fragrance notes of a particular fixative are then further evaluated on the basis of relative strength or dominance. The olfactory profiles of three common fixatives are compared on the basis of relative note dominance in Table 1b. A balanced combination of fixatives, covering the range of notes, works best for general usage.

TABLE 1

| OLFACTORY PROFILE OF SELECTED FIXATIVES | | | | | | | | |
|---|---|---|---|---|---|---|---|---|
| CHARACTERISTIC FRAGRANCE NOTE | 1 | 2 | 3 | 4 | 5 | 6 | 7 | 8 |
| Citrus |   |   |   |   |   | + |   |   |
| Fresh |   |   | + |   |   |   | + |   |
| Earthy |   |   |   |   |   |   | + |   |
| Fruity |   |   | + |   |   |   |   |   |
| Animal | + | + | + | + |   |   | + | + |
| Floral | + |   | + |   | + |   | + | + |
| Sweet | + | + | + | + | + | + | + | + |
| Spicy |   |   |   |   |   | + |   |   |
| Powdery |   |   | + |   |   |   | + | + |
| Amber |   |   | + |   | + | + | + | + |
| Woody |   |   |   |   | + |   | + | + |
| Balsamic |   |   |   |   |   |   | + |   |

| OLFACTORY RELATIVE DOMINANCE OF NOTE | | | |
|---|---|---|---|
| CHARACTERISTIC FRAGRANCE NOTE | 3 | 7 | 8 |
| Fresh | -- | - |   |
| Earthy |   | -- |   |
| Fruity | -- |   |   |
| Animal | -- | -- | -- |
| Floral | --- | - | -- |
| Sweet | -- | -- | -- |

TABLE 1-continued

| | | | |
|---|---|---|---|
| Spicy | - |   |   |
| Powdery | --- | --- | --- |
| Amber | ---- | ---- | --- |
| Woody |   | --- | - |
| Balsamic | - |   |   |

---- strong dominant note
--- important secondary note
-- clearly noticeable background note
- barely noticeable note Key:
1. Ethylene brassylate (Musk T, Takasago)
2. 4-acetyl-6-t-butyl-1,1-dimethylindane (Celestolide, IFF)
3. 11-Oxahexadecanolide (Musk R-1, Naarden)
4. 1,3,4,6,7,8-hexahydro-4,6,6,7,8,8-hexamethyl-cyclopenta-gamma-2-benzopyran (Galaxolide, IFF)
5. 6-t-Butyl-3-methyl-2,4-dinitroanisole (Musk ambrette, Givaudan)
6. 1,1,4,4-Tetramethyl-6-ethyl-7-acetyl-1,2,3,4-tetrahydronaphthalene (Versalide, Givaudan)
7. Ambergris
8. Cervolide ™ (Naarden)

Fixatives that are chemical homologues of one another may have the same olfactory profile but have different strengths or potencies. For example, Carpenter, M. and Easter, W. *J. Organic Chemistry* 16:618–620 (1951) found that homologues of the nitro musks Musk xylene and Musk ketone, as well as others of this group, having the tert-butyl group replaced by tert-amyl, had the same musk nuance of their prototype, but in diminished intensity. This range of intensity is also useful in formulation of the compositions of the invention. For example, a strong cologne requires a lesser concentration or a weaker fixative to achieve the desired effect of prolonging and enriching the fragrance, whereas a more subtle cologne might require a higher concentration or a more potent fixative. In preferred embodiments, the concentrations of these fixative materials can be as low as 0.1% and as high as 50%, depending on the particular fixative or combination of fixatives vis-a-vis the cologne or eau de toilette it is to be used upon.

A variety of organic solvents can be used as the vehicle for dissolving and delivering the particular combination of fixatives. A suitable solvent will be non-reactive with the fixative. Further, in order to achieve the desired effect the solvent should be volatile. The solvent should further be compatible with fragrance materials in an olfactory sense, that is, it should be odorless, or have an odor which blends with most fragrance materials. Solvents having these characteristics include, but are not limited to, ethanol, volatile silicones, such as cyclomethicones and phenyltrimethicones, diethyl phthalate, and benzyl benzoate. A preferred solvent is ethanol. In alternative embodiments, solvents may be used in combination to achieve a desired result.

Preferred fixative agent solution compositions are listed in Examples 1 and 4. Another preferred fixative solution is comprised of 1.0 g musk ketone, 1.0 g civetone and 98.0 g ethanol (39C). Still another preferred solution comprises 0.5 g musk ambrette, 0.5 g musk xylol, 49.0 g silicone fluid 556 (Dow Corning) and 50.0 g ethanol (39C).

The fixative is most preferably applied to a person or his clothing in the same manner as the fragrance. In a most convenient form, the fixative is applied by spraying a measured amount of the fixative solution. Preferably this solution is packaged in a spray container that delivers 100 mg of solution per spray. In an alternate preferred embodiment, the fixative is applied with an absorbent material or with the hands. In another preferred embodiment, the method is used on surfaces other than human skin, such as clothing. In one embodiment, the method is to be used only with a commercially available eau de toilette, after shave, toilet water, eau de cologne, or cologne. The fixative solution can be applied before, concurrently with, or after the application of the fragrance.

The advantages of the fragrance-enhancing fixative preparations of the invention are that when they are applied together with a cologne, the effect of the combination is that of the more expensive fragrance form, and the scent persists longer, achieving an overall economy. Another attractive feature is that one fragrance-enhancing preparation comprising fixatives with a broad olfactory profile will enhance a broad range of scent products, so that multiple preparations are not necessary. The use of the fragrance enhancing preparations of the invention will allow the user to adjust the strength and lasting power of a fragrance form to suit his or her own preferences. The use of these preparations will also obviate the need for frequent re-applications of a fragrance throughout the day. Moreover, they are easily and conveniently applied.

The present invention is illustrated by means of the following Examples, which are not intended to be unduly limiting, since the principles set forth herein are broadly applicable to the preparation of a wide variety of formulations.

EXAMPLE 1

Blind Comparison of Enhancing Activity

In a blinded test conducted with the solution below, the forearms of six subjects were cleansed with alcohol swabs, and after drying, were sprayed with equal amounts (one spray) of Chanel No. 5 cologne. Then one arm was oversprayed with one spray (100 mg) of the solution and the other was oversprayed with an equal amount of a placebo spray consisting of 100% ethanol 39C.

Solution Composition
  0.625 g. galaxolide (IFF)
  1.25 g. ethylene brassylate
  1.25 g. 4-acetyl-6-t-butyl-1,1-dimethylindane
  1.25 g. 11-oxahexadecanolide
  0.625 g. diethyl phthalate
  95.0 g. ethanol (39C)

Subjects compared the scent of each arm at 1, 3, 5, 7, and 10 hours after application for strength and fullness. In 74.2% of the evaluations, the side treated with the above solution was judged to be stronger and fuller. An objective evaluation was performed by a blinded independent expert at 1, 3, 5, and 7 hours after application. In 62.5% of the cases he discerned that the side treated with the above solution to be stronger and fuller. In both the evaluations by the subjects and those by the expert, each judging was independent in that the evaluator did not have access to his previous evaluations.

EXAMPLE 2

Expert Evaluation

In another evaluation of the method, contralateral forearm sites of an expert evaluator were cleansed with alcohol swabs and then sprayed with equal amounts of Sandalwood Mens Spray Cologne. The left side was oversprayed with 100 mg of the fixative solution described in Example 1. Olfactory evaluations were done at 15 min., 1, 2, 4, and 6 hours. At 15 minutes, both sides were judged to be the same. At all other times, the left side was judged to be significantly stronger and more fullbodied, while maintaining the original character of sandalwood. This experiment was then repeated using Obsession Cologne in place of Sandalwood. The results were identical, e.g., no differences were noted at 15 minutes, but at all other times there were significant differences between treated and untreated sites. The character of the cologne remained uncharged on the treated side in spite of the increase in strength and fullbodiedness.

EXAMPLE 3

Double Blind Field Study: 67 Subjects

In a further evaluation of the previously described preferred embodiment, contralateral forearm sites of 67 college students were cleansed with alcohol swabs, dried, and then sprayed with equal amounts of Chanel No. Cologne. Then, according to a randomized schedule, each arm was sprayed with either the fixative solution described in Example or an equal amount of a placebo comprising 100% ethanol (39C). After five hours, 60% of the subjects that discriminated a difference reported that the treated side was more intense; 61% reported that the treated side smelled richer and more full-bodied.

EXAMPLE 4

Another preferred embodiment of the fixative agent solution comprises:
  0.25 g. galaxolide (IFF)
  0.50 g. ethylene brassylate
  0.50 g. 4-acetyl-6-r-butyl-1,1-dimethylindane
  0.50 g. 11-oxahexadecanolide
  0.25 g. diethyl phthalate
  98.0 g. ethanol (39C)

In a blinded test of this embodiment, the contralateral forearm sites of an expert evaluator were cleansed with alcohol swabs and then sprayed with equal amounts of Obsession Cologne. The left side was oversprayed with 100 mg of the foregoing fixative solution. Olfactory evaluations were done at 15 min, 1, 2, 4, and 6 hours. The evaluator detected a significant improvement in the strength and body of the treated cologne application sites at all test times except the 15 minute evaluation.

Although the invention has been described in the context of certain preferred embodiments, it is intended that the scope of the invention not be limited to the specific embodiments set forth herein, but instead be measured by the claims that follow.

APPENDIX
Representative Members of Fixative Classes

A: NITRO MUSKS

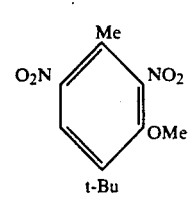

Musk Ambrette
(6-t-butyl-3-methyl-2,4-dinitroanisole)

-continued
APPENDIX
Representative Members of Fixative Classes

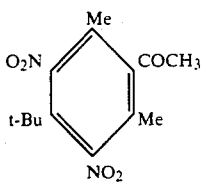

Musk Ketone
(4-t-butyl-3,5-dinitro-2,6-dimethylacetophenone)

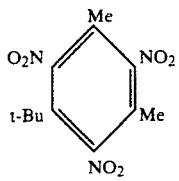

Musk Xylol
(2,4,6-trinitro-1,3-dimethyl-5-t-butylbenzene)

B: MACROCYCLICS

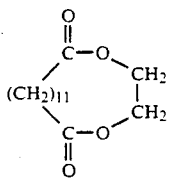

Ethylene brassylate
(5,17-diketo-1,4-dioxa-cycloheptadecane)

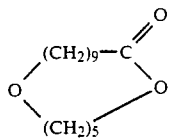

11-oxahexadecanolide

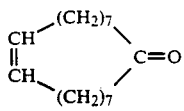

Civetone
(9-cycloheptadecene-1-one)

C: HYDROAROMATIC POLYCYCLICS

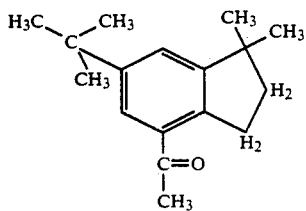

4-acetyl-6-t-butyl-1,1-dimethylindane

-continued
APPENDIX
Representative Members of Fixative Classes

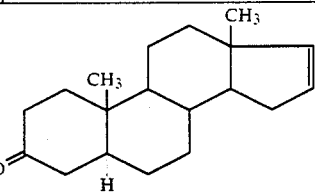

16-androsten-3-one

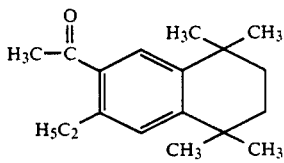

(1,1,4,4-tetramethyl-6-ethyl-7-acetyl-1,2,3,4-tetrahydronaphthalene)

D: OXAHYDROAROMATICS

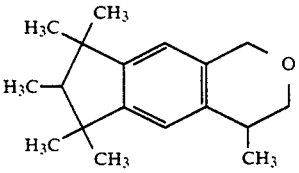

Galaxolide (1,3,4,6,7,8-hexahydro-4,6,6,7,8,8-hexamethyl-cyclopenta-γ-2-benzopyran)

What is claimed is:

1. A method for enhancing the olfactory effect and persistence of an applied fragrance form, comprising:
applying a composition consisting essentially of one or more fixative agents selected from the group consisting of nitro musks, macrocyclic, hydroaromatic polycyclic, or oxahydroaromatic compounds, or combinations thereof, in a suitable volatile solvent, to the surface of an object to be scented;
separately applying to said surface a fragrance solution, so that said separately applied fragrance and fixative coexist on said surface.

2. The method of claim 1, wherein a solution of said fixative agent is applied by overspraying the applied fragrance form.

3. The method of claim 1, wherein said fragrance form is applied to human skin.

4. The method of claim 1, wherein said fragrance is in the form of a commercial eau de toilette, after shave, toilet water, eau de cologne, eau de parfum, or eau de perfume.

5. The method of claim 1, wherein said fixative agent is selected from the group consisting of galaxolide, ethylene brassylate, 4-acetyl-6-tert-butyl-1,1-dimethylindane, 11-oxahexadecanolide, musk ambrette, musk ketone, musk xylol, civetone or, androstene-one and combinations thereof.

6. The method of claim 1, comprising the co-application of a mixture of galaxolide, ethylene brassylate, 4-acetyl-6-tert-butyl-1,1-dimethylindane, and 11-oxahexadecanolide in a ratio of 1:2:2:2 by weight.

7. The method of claim 5 wherein said volatile solvent is ethanol, a volatile silicone, diethyl phthalate, benzyl benzoate, or a mixture thereof.

8. The method of claim 1, further comprising the step of allowing solvent of the first-applied solution to evaporate from said surface to a substantial degree before applying the other solution.

9. The method of claim 1 or 8, wherein a fragrance solution is first applied to said surface.

* * * * *

UNITED STATES PATENT AND TRADEMARK OFFICE
CERTIFICATE OF CORRECTION

PATENT NO. : 5,120,709
DATED : June 9, 1992
INVENTOR(S) : Cella et al.

It is certified that error appears in the above-indentified patent and that said Letters Patent is hereby corrected as shown below:

Column 2, line 13, after "from", delete ":".

Column 3, line 42, after "ethylene", "brassylate" should be so written.

Column 4, line 2, after "to", please delete "creates" and replace it with --create--.

Column 8, line 6, please delete "uncharged" and replace it with --unchanged--.

Column 8, line 18, after "No.", --5-- should be inserted.

Column 8, line 20, after "Example", --1-- should be inserted.

Signed and Sealed this

Twenty-first Day of September, 1993

Attest:

BRUCE LEHMAN

Attesting Officer        Commissioner of Patents and Trademarks